United States Patent [19]

Ataka et al.

[11] Patent Number: 5,030,755

[45] Date of Patent: Jul. 9, 1991

[54] PROCESS FOR PRODUCING SUBSTITUTED PHENOXYETHYLAMINES AND INTERMEDIATES

[75] Inventors: Kikuo Ataka; Koji Imaoka; Kiyotaka Yoshii, all of Ube; Kenji Hirotsu, Oaza Kogushi, all of Japan

[73] Assignees: Ube Industries Ltd., Ube; Sankyo Co., Ltd., Tokyo, both of Japan

[21] Appl. No.: 604,757

[22] Filed: Oct. 26, 1990

Related U.S. Application Data

[62] Division of Ser. No. 397,179, Aug. 21, 1989, Pat. No. 4,985,596.

[30] Foreign Application Priority Data

Aug. 30, 1988 [JP] Japan .................... 63-213636

[51] Int. Cl.$^5$ ........................................ C07C 251/40
[52] U.S. Cl. ............................ 564/265; 564/253; 564/258; 564/354
[58] Field of Search ........................................ 564/265

[56] References Cited

U.S. PATENT DOCUMENTS

| | | | |
|---|---|---|---|
| 2,644,822 | 7/1953 | Pearl | 564/265 |
| 3,429,920 | 2/1969 | DeRooji | 564/259 |
| 3,655,761 | 4/1972 | Gutman | 564/259 |
| 3,780,104 | 12/1973 | Teach | 71/100 |
| 3,890,134 | 6/1975 | Teach | 71/100 |
| 4,323,706 | 4/1982 | Bonfield et al. | 564/259 |
| 4,845,097 | 7/1989 | Matsumoto et al. | 514/234.2 |
| 4,864,061 | 9/1989 | Cohnen | 564/349 |

FOREIGN PATENT DOCUMENTS

| | | | |
|---|---|---|---|
| 1934014 | 5/1970 | Fed. Rep. of Germany . | |
| 1537206 | 8/1968 | France . | |
| 49-02105 | 1/1974 | Japan . | |
| 61-260054 | 11/1986 | Japan . | |
| 222753 | 1/1987 | Japan | 564/256 |
| 233143 | 2/1987 | Japan | 564/256 |
| 320657 | 8/1988 | Japan | 564/256 |
| 1256764 | 12/1971 | United Kingdom . | |

OTHER PUBLICATIONS

Chemical Abstracts, vol. 81, No. 21, Nov. 25, 1974, p. 390, abstract No. 13572k, Columbus, Ohio, U.S.; & JP-A-74-02105 (correctly 49-02105), Sumitomo Chemical Co., Ltd. 1974.

Hannele Salomies, Studies on the Oxidation of B—Blocking Agents With Sodium Metaperiodate and N—Bromosuccinimide, Annales Academiae Scientiarum Fennicae, Ser. A, II. Chemica, 216, 1988.

(List continued on next page.)

Primary Examiner—Glennon H. Hollrah
Attorney, Agent, or Firm—Frishauf, Holtz, Goodman & Woodward

[57] ABSTRACT

Disclosed are a process for producing a substituted phenoxyacetaldehyde oxime of the formula:

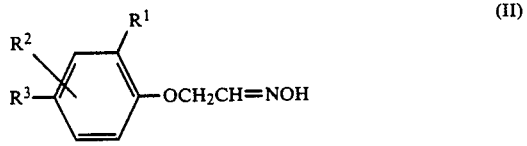

(II)

(wherein $R^1$, $R^2$ and $R^3$ are as defined in the specification), which comprises allowing a substituted phenoxyacetaldehyde dialkylacetal of the formula:

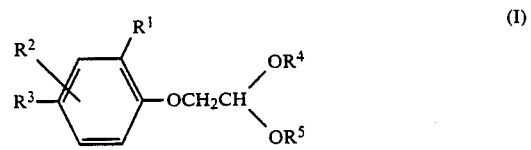

(I)

(wherein $R^1$, $R^2$, $R^3$, $R^4$ and $R^5$ are as defined in the specification) to react with hydroxylamine; a process for producing a substituted phenoxyethylamine of the formula:

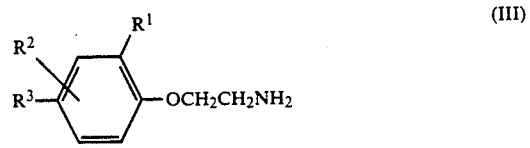

(III)

(wherein $R^1$, $R^2$ and $R^3$ are as defined in the specification), which comprises reducing a substituted phenoxyacetaldehyde oxime of the formula (II) with hydrogen in the presence of a Raney-nickel catalyst; and a substituted phenoxyacetaldehyde oxime of the formula:

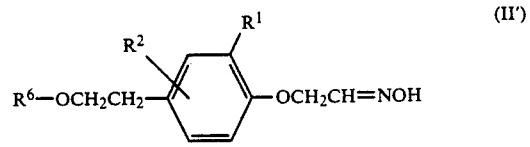

(II')

(wherein $R^1$, $R^2$ and $R^6$ are as defned in the specification).

10 Claims, No Drawings

OTHER PUBLICATIONS

Chem. Abstracts 92 (3) 22184q Khim. Prom-St., Ser.; Reakt. Osobo Chist. Ves. chestva (2) 1-3.

Teruaki Mukaiyama et al., A Novel Method for the Preparation of Primary Amines by the Use of N-Benzylhydroxylamine and 2-Fluoropyridinium Salt, Chem. Lett., 10, (1978) 1057-1060.

A. C. Knipe et al., Desulphonative Double Smiles' Rearrangements of N-(2-Hydroxyalkyl)p-Nitrobenzene Sulphonamides in Aqueous Alkali: Isolation of Intermediate 2-(p-Nitrophenoxy)Alkylamines, Tetrahedron Lett., 26 1976 2289-2290.

K. Wimalasena et al., Mechanistic Studies on Dopamne $\beta$-oxygenase Catalysis: N-Dealkylation and Mechanism-Based Inhibitio by Benzylic-Nitrogen-Containing Compounds, J. Amer. Chem. Soc., 109 4036-4046 (1987).

Niwa et al., Development of (Phenoxyphenoxy) and (Benzylphenoxy) Alkanaldoxime O-Ethers as Potent Insect Juvenile Hormone Munics and Their Quantitative Structure-Activity Relationship, J. Agric. Food Chem. 1988, 36, 378-384.

King and Robinson: Experiments on the Synthesis of Physostigmine (Eserine) J. Chem. Soc. 1933, pp. 270-273.

Leallyn B. Clapp, Reactions of Ethylenimines with Phenols, J. Amer. Chem. Soc., 73 (1951), pp. 2584-2586.

Chem. Abstracts 1961, 2537, Roczniki Chem. 32, 661-6(1958).

PROCESS FOR PRODUCING SUBSTITUTED PHENOXYETHYLAMINES AND INTERMEDIATES

This is a division of application Ser. No. 07/397,179 filed Aug. 21, 1989 now U.S. Pat. No. 4,985,596.

BACKGROUND OF THE INVENTION

This invention relates to a process for producing substituted phenoxyethylamines, intermediates for synthesis of said amines and a process for producing said intermediates. Substituted phenoxyethylamines are useful as synthetic intermediates for substituted phenoxyethyl-aminopyrimidine derivatives exhibiting high activities as insecticides, acaricides (Japanese Unexamined Patent Publications Nos. 3667/1984 and 67/1987).

In the prior art, as the process for synthesizing substituted phenoxyethylamines, there have been known the processes shown by the following reaction schemes. In the formulae, Ar represents an aryl group.

$$ArOCH_2CH_2Br + NH_3 \longrightarrow ArOCH_2CH_2NH_2 \quad (1)$$

Chem. Ber. 70 (1937) 979

$$ArOK + ClCH_2CH_2NH_2 \longrightarrow ArOCH_2CH_2NH_2 \quad (2)$$

J. Pharm. Soc. Japan 63 (1943) 546

$$ArOCH_2CONH_2 + LiAlH_4 \longrightarrow ArOCH_2CH_2NH_2 \quad (3)$$

Helv. Chemica Acta. 31 (1948) 1397

$ArOCH_2CH_2Br$ + potassium phthalimide (4) $ArOCH_2CH_2Br$ + potassium phthalimide

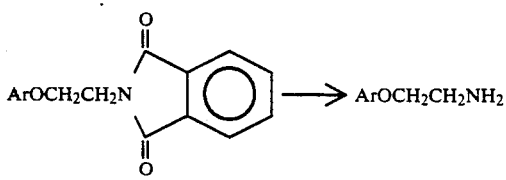

J. Chem.Soc. 1933, p.270, U.S. Pat. No. 3,474,134

$$ArOH + \text{ethyleneimine} \longrightarrow ArOCH_2CH_2NH_2 \quad (5)$$

J. Amer. Chem. Soc., 73 (1951) 2584

$$ArOCH_2CH_2NH_2 + \text{hexamethylenetetramine} \longrightarrow ArOCH_2CH_2NH_2 \quad (6)$$

Roczniki Chem. 661(1958), C.A. 1961, 2537

$$NH_2CH_2CH_2OK + ArX \longrightarrow ArOCH_2CH_2NH_2 \quad (7)$$

Khim. Prom-St., Ser.; Reakt.Osobo Chist. Ves chestva (2) 1–3 C.A. 92 (3) 22184q $$RCH_2NHOH + R'X \longrightarrow RCH_2NHOR' \longrightarrow RCH=NR' \longrightarrow R'NH_2 \quad (8)$$

Chem. Lett., 10, 1057

$$ArSO_2NHCH_2CH_2OH + NaOH \longrightarrow ArOCH_2CH_2NH_2 \quad (9)$$

Tetrahedron Lett., 26 2289

$$ArOCH_2CN + LiAlH_4 \longrightarrow ArOCH_2CH_2NH_2 \quad (10)$$

J. Amer Chem. Soc., 109 4036 (1987)

$ArOCH_2CH_2Br$, which is starting material of the above processes of (1), (4) and (6), can be synthesized only in poor yield because of producing much by-products.

The above processes of (1), (4) and (6) produce much byproducts during synthesis of $ArOCH_2CH_2Br$, and are poor in yield. The reactions for introducing a substituent into Ar group suffer from many restrictions due to the presence of halogen substituents, and the desired substituted phenoxyethylamines cannot be produced in most cases. The processes of (2) and (5) are extremely poor in yield. The processes of (3) and (10) are not suitable for commercial application because $LiAlH_4$ is expensive. The process of (7) is dangerous in handling and also expensive, because metallic potassium is used. The process of (8) cannot extend in commercial scale because expensive reagents are used. The process of (9) is defective in that the reaction does not proceed unless the substituent on Ar is p-nitro or the like.

As described above, various problems have been involved in commercial application of the prior art processes Although the process for producing oxime derivatives from corresponding aldehydes has not been known in the art, the reaction with hydroxylamine-O-alkyl ether is disclosed in Japanese Unexamined Patent Publication No. 260054/1986. When the compounds of the present invention were adapted to be produced by this process, much by-products were formed to give poor yield. Also, when hydroxylamine sulfate, which is advantageous in commercial availability, handling, corrosiveness, etc., was used, there ensued the problem that substantially no reaction proceeded.

SUMMARY OF THE INVENTION

In view of these situations, the present invention is intended to provide a synthetic intermediate for producing substituted phenoxyethylamines simply and inexpensively, and also to provide a process for production thereof.

The present inventors have investigated intensively in order to accomplish the above objects, and consequently found that substituted phenoxyethylamines can be produced by far more easily, inexpensively and on an industrial scale as compared with the prior art process by using oximes as an intermediate, to accomplish the present invention.

The process of the present invention is a process for producing a substituted phenoxyacetaldehyde oxime of the formula:

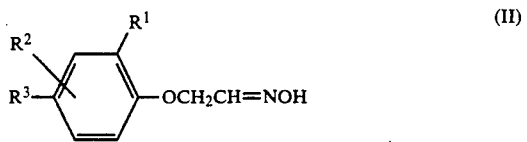

[wherein $R^1$ and $R^2$ each represent a hydrogen atom or a lower alkyl group, $R^3$ represents a hydrogen atom or a $-CH_2CH_2O-R^6$ group (here, $R^6$ is a hydrogen atom or a lower alkyl group)], which comprises allowing a substituted phenoxyacetaldehyde dialkylacetal of the formula:

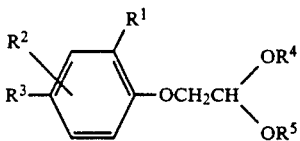

(wherein $R^1$, $R^2$ and $R^3$ have the same meanings as defined above, $R^4$, and $R^5$ each represent a lower alkyl group) to react with hydroxylamine, and a process for producing a substituted phenoxyethylamine of the formula:

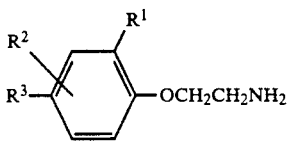

(wherein $R^1$, $R^2$ and $R^3$ have the same meanings as defined in the above), which comprises reducing a substituted phenoxyacetaldehyde oxime of the formula:

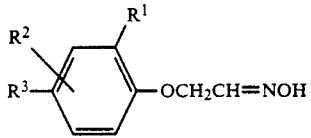

(wherein $R^1$, $R^2$ and $R^3$ have the same meanings as defined above) with hydrogen in the presence of a Raney-nickel catalyst.

Further, the present invention is a substituted phenoxyacetaldehyde oxime of the formula:

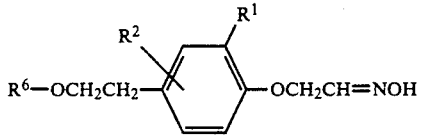

(wherein $R^1$, $R^2$ and $R^6$ have the same meanings as defined in claim 1), which is a novel intermediate compound.

DETAILED DESCRIPTION OF THE INVENTION

In the first step of the present invention, the acetals (I) of the starting material can be produced easily according to the process similar to that as described in Japanese Unexamined Patent Publication No. 313743/1988.

As hydroxylamine, its mineral acid salt, for example, sulfate, hydrochloride, etc. may be available. Its amount used may be 0.5 to 3.0-fold mols, preferably 1.0 to 2.0-fold mols per acetals (I).

As the reaction solvent, water, methanol, ethanol, etc. may be preferable, more preferably mixtures of these. The solvent may be used so that the concentration of acetals (I) employed may be within the range of 5 to 50%. The reaction temperature may be preferably within the range of 50° to 70° C., and the reaction will be substantially completed within 3 to 18 hours.

In this case, the pH of the reaction mixture is an important factor for yield. Preferable pH is within the range of 1.0 to 0.1, particularly 0.5 to 0.3 to give good yield. The pH is adjusted at the pH range with a mineral acid such as dil. sulfuric acid, dil. hydrochloric acid (1 to 12 N) before the reaction. Because pH is lowered with progress of the reaction, it is preferable to add dropwise an aqueous solution of an alkali metal hydroxide (1 to 12 N) such as sodium hydroxide as occasion demands. If the pH is higher than this setting pH, the reaction will not proceed, while if it is lower, by-products will be formed in a large amount to lower the yield.

In the course of the reaction or after completion of the reaction, when the mixture is cooled, oximes (II) are precipitated as the solid This can be isolated by conventional method such as filtration, etc. Only by washing the solid with water, followed by drying, substantially pure oximes (II) can be obtained When the oximes (II) produced are liquid, crude oximes (II) can be obtained by extraction with an appropriate solvent As the extraction solvent, any solvent which can dissolve oximes (II) and is insoluble in water may be available Chlorinated hydrocarbons such as methylene chloride, chloroform, dichloroethane, etc., ether compounds such as ethyl ether, isopropyl ether, butyl ether, etc. are preferred. The crude product can be purified by the purification method such as chromatography or by washing with a solvent in which oximes (II) cannot be dissolved (preferably hydrocarbon solvents such as hexane, benzene, toluene, etc.). The oximes (II) thus obtained are mixtures of synanti geometric isomers, and either isomer is included in the present invention.

Specific examples of oximes (II) may include:
2-[4-(2-ethoxyethyl)phenoxy]-acetaldehyde oxime;
2-[4-(2-ethoxyethyl)-2-methylphenoxy]-acetaldehyde oxime;
2-[4-(2-ethoxyethyl)-2-ethylphenoxy]-acetaldehyde oxime;
2-[2,3-dimethyl-4-(2-ethoxyethyl)phenoxy]-acetaldehyde oxime;
2-[2,5-dimethyl-4-(2-ethoxyethyl)phenoxy]-acetaldehyde oxime;
2-[2,6-dimethyl-4-(2-ethoxyethyl)phenoxy]-acetaldehyde oxime;
2-[4-(2-methoxyethyl)-2-methylphenoxy]-acetaldehyde oxime;
2-[2-ethyl-4-(2-methoxyethyl)phenoxy]-acetaldehyde oxime;
2-[2,3-dimethyl-4-(2-methoxyethyl)phenoxy]-acetaldehyde oxime;
2-[2,5-dimethyl-4-(2-methoxyethyl)phenoxy]-acetaldehyde oxime;
2-[2,6-dimethyl-4-(2-methoxyethyl)phenoxy]-acetaldehyde oxime;
2-[4-(2-hydroxyethyl)phenoxy]-acetaldehyde oxime;
2-[4-(2-hydroxyethyl)-2-methylphenoxy]-acetaldehyde oxime;
2-[2-ethyl-4-(2-hydroxyethyl)phenoxy]-acetaldehyde oxime;
2-[2,3-dimethyl-4-(2-hydroxyethyl)phenoxy]-acetaldehyde oxime;
2-[2,5-dimethyl-4-(2-hydroxyethyl)phenoxy]-acetaldehyde oxime;
2-[2,6-dimethyl-4-(2-hydroxyethyl)phenoxy]-acetaldehyde oxime;
2-phenoxyacetaldehyde oxime, and the like Of the above oximes (II), the compounds of the above formula (II') are novel In the above formula, the lower alkyl group represented by $R^1$, $R^2$ and $R^6$ may be, for example, methyl, ethyl, propyl, and particularly the compound wherein $R^1$ is methyl, $R^2$ is 3-methyl and $R^6$ is ethyl is preferred. The lower alkyl group represented by $R^4$ and $R^5$ may be, for example, methyl, ethyl, propyl and butyl The present invention is also the method of the second step of producing the amines (III) from the oximes (II).

For the reaction of reducing an oxime with hydrogen, used as the catalyst are palladium, platinum, Raney nickel, etc. Particularly, there are many examples of palladium type catalysts with low hydrogen pressure during the reaction Various catalysts have been investigated for producing oximes (II), and consequently no desired product could be obtained using a palladium type catalyst under neutral conditions, but only side reaction products were obtained. The same was the case with platinum catalysts And, only when a palladium type catalyst was used under acidic conditions, the salt of the desired product was obtained, although in low yield Even with Raney catalyst, Raney cobalt was low in yield With other catalysts, no desired product could be produced or the desired product could be produced at very low yield within generally feasible pressure and temperature ranges. Whereas, it has been found that only Raney nickel catalyst reduces specifically oximes (II) selectively.

The reaction is carried out in an autoclave, because it is generally carried out under hydrogen pressure Better results can be given as the hydrogen pressure is higher, but good results can be given generally within the pressure range of 20 to 150 atm. The yield will be extremely lowered at a pressure lower than 10 atm.

As the reaction solvent, alcoholic solvents such as methanol, ethanol, etc. are suitable The reaction temperature is required to be 40° C. or higher, generally within the range of 60° to 200° C.

The concentration of the oximes (II) may be generally 1 to 60% by weight for carrying out the reaction, but preferably within the range of 5 to 30% when considering yield and economy. At higher concentration, side reactions are liable to occur.

The reaction may be feasible with an amount of Raney nickel which may be 0.2 to 30% by weight as the nickel amount based on the oximes (II), more preferably within the range of 5 to 20% by weight As the kind of Raney nickel, conventional Raney nickel, 20 to 50%Ni - Al alloy containing added metals such as Cr, Mo, etc. can be used. Also, use of a stabilized nickel is possible Although yield is not greatly affected by the developing method of Raney nickel, but the method of W-6 gave the best result. Of course, sufficient activity can be also exhibited by other developing methods.

As the additive during the reaction, ammonia and tertiary amines have the effect As tertiary amines, trimethylamine, triethylamine, etc. may be available When no such additive exists, secondary amines other than the desired amine will be by-produced, but its amount is little and the addition is not essential The amount of ammonia, tertiary amine added may be preferably 0.01 to 1.0-fold weight based on the oximes (II), and if added in excess of this range, another side reaction is promoted to lose its effect For further improving the yield of the present reaction, the activation operation of the catalyst is very effective. The activation operation is an operation which permits the catalyst to contact to hydrogen under the reaction conditions in the absence of the oximes (II) prior to the reaction of the oximes (II) with the catalyst The present operation is carried out generally under the conditions of 10 atm. to the hydrogen pressure under the reaction conditions, at 80° to 100° C. for 0.2 to 2 hours in the presence of a catalyst in a solvent with stirring. The additive of ammonia, etc. may be also present After the operation, oximes (II) are suspended or dissolved in the same solvent, and charged into the autoclave. The reaction is initiated by setting the reaction temperature and pressure Not only yield is improved, but reproducibility of the reaction becomes very good by this operation. The catalyst provided for the reaction is reusable, and the effect of the present activation operation was also recognized in the recycle reaction of the catalyst separated by filtration or decantation.

After completion of the reaction, the catalyst is removed by releasing pressure, cooling, followed by filtration. The filtrate is concentrated and the desired substituted phenoxyethylamine (III) can be obtained as the crude product. The crude product can be purified by distillation or formation of a salt with a mineral acid. The mineral acid salts of the substituted phenoxyethylamines (III) are almost insoluble in an organic solvent and therefore can be readily obtained by reacting it with a mineral acid in an organic solvent Since the mineral acid salts readily liberate the substituted phenoxyethylamines (III) by contact with an aqueous alkali solution such as sodium hydroxide, potassium hydroxide, etc., substituted phenoxyethylamines (III) of high purity can be obtained according to conventional procedures such as liquid separation, extraction, etc.

Examples of substituted phenoxyethylamines (III) may include:

2-[4-(2-ethoxyethyl)phenoxy]-ethylamine;
2-[4-(2-ethoxyethyl)-2-methylphenoxy]-ethylamine;
2-[4-(2-ethoxyethyl)-2-ethylphenoxy]-ethylamine;
2-[2,3-dimethyl-4-(2-ethoxyethyl)phenoxy]-ethylamine;
2-[2,5-dimethyl-4-(2-ethoxyethyl)phenoxy]-ethylamine;
2-[2,6-dimethyl-4-(2-ethoxyethyl)phenoxy]-ethylamine;
2-[4-(2-methoxyethyl)phenoxy]-ethylamine;
2-[4-(2-methoxyethyl)-2-methylphenoxy]-ethylamine;
2-[2-ethyl-4-(2-methoxyethyl)phenoxy]-ethylamine;
2-[2,3-dimethyl-4-(2-methoxyethyl)phenoxy]-ethylamine;
2-[2,5-dimethyl-4-(2-methoxyethyl)phenoxy]-ethylamine;
2-[2,6-dimethyl-4-(2-methoxyethyl)phenoxy]-ethylamine;
2-[4-(2-hydroxyethyl)phenoxy]-ethylamine;
2-[4-(2-hydroxyethyl)-2-methylphenoxy]-ethylamine;
2-[2-ethyl-4-(2-hydroxyethyl)phenoxy]-ethylamine;
2-[2,3-dimethyl-4-(2-hydroxyethyl)phenoxy]-ethylamine;
2-[2,5-dimethyl-4-(2-hydroxyethyl)phenoxy]-ethylamine;
2-[2,6-dimethyl-4-(2-hydroxyethyl)phenoxy]-ethylamine;
2-phenoxyethylamine; and the like Referring now to Examples, the present invention is described in more detail.

EXAMPLE 1

2-[2,3-Dimethyl-4-(2-ethoxyethyl)phenoxy]-acetaldehyde oxime

A mixture of 2.1 liters of methanolic solution of 760 g of 1-(2,2-dimethoxyethoxy)-4-(2-ethoxyethyl)-2,3- dimethylbenzene and 2 1 liters of aqueous solution of 466 g of hydroxylamine sulfate was heated to 70° C. To the mixture added was 12 N sulfuric acid until the pH became 0.5, and the mixture was stirred vigorously. Since the pH is lowers with the progress of the reaction, an aqueous 12 N sodium hydroxide solution was added dropwise so as to maintain pH at 0.5. The reaction was monitored by HPLC, and when the conversion exceeded 95%, the reaction mixture was cooled to around room temperature. Generally, the reaction requires about 10 hours. After pH was adjusted to 6.5 with 12 N-NaOH, the solid formed was filtered The filtered product was washed with 1.0 liter of warm water, and dried under reduced pressure to obtain the title product. m.p. 102°–105° C., amount obtained 676 g, purity 93%, yield 93%.

Proton NMR ($\delta$, CDCl$_3$-DMSO-d$_6$): 1.2 (t,3H,C-CH$_3$), 2.2–2.25 (6H,ArCH$_3$, 4 peaks were observed according to syn-anti isomers), 2.8 (t,2H,Ar-CH$_2$), 3.4–3.6 (two sets of d,4H,CHHD 2OC$_2$), 4.55, 4.8 (d,2H,—CH$_2$—C=N, according to syn-ant isomer), 6.67(t,lH,ArH, according to syn-anti isomer), 6.92 (d,lH, ArH), 6.89, 7.51 (t, total IH, —CH=N, according to syn-anti isomer), 10.93, 11.15 (s,br,total IH,-NOH).

EXAMPLE 2

2-[2,5-dimethyl-4-(2-ethoxyethyl)phenoxy]-acetaldehyde oxime was synthesized similarly as in Example 1.

Colorless solid. m.p. 66°–70° C., yield 87%

EXAMPLES 3 to 8

Similarly as in Example 1, but on a scale of 1/100, the following compounds were synthesized. However, when the product was liquid, it was not isolated by filtration, but extracted with 50 ml of methylene chloride, followed by drying, concentration and, if desired, purification by column chromatography to obtain the product.

Conditions of column chromatography: Wako Gel C200, Eluant: n-hexane:ethyl acetate=5:1.

EXAMPLE 3

2-[2,6-dimethyl-4-(2-methoxyethyl)phenoxy]-acetaldehyde oxime

Pale yellow oil, yield 91%.

Proton NMR ($\delta$, CDCl$_3$): 2.25 (s,6H,ArCH$_3$), 2.75(t,2H,ArCH$_2$), 3.35(s,3H,-OCH$_3$), 3.58 (t,2H,CHHD 2—OMe), 4.40, 4.67 (respectively d, total 2H, CH$_2$C=N, according to syn-anti isomer), 6.85 (s,2H,ArH), 7.15, 7.69 (respectively t, total IH, —CH=N, according to syn-anti isomer), 7.65, 7.9 (s,br,total IH, n=OH).

Example 4

2-[4-(2-Ethoxyethyl)-2-ethylphenoxy]-acetaldehyde oxime

Pale yellow oil, yield 85%.

Proton NMR ($\delta$, CDCl$_3$): 1.1–1.3 (m,6H,ArCH$_2$CHHD 3, according to syn-anti isomer), 2.55–2.7 (m,2H,ArCHHD 2Me), 2.8 (t,2H,Ar-CHHD 2CH$_2$—O), 3.51 (q,2H, OCHHD 2CH$_3$), 3.60 (t,2H,ArCH$_2$CHHD 2—O), 4.52, 4.90 (respectively d,total 2H,OCH$_2$=CN, according to syn-anti isomer), 6.7–7.1 (m about 3.5 H, peak of both syn and anti isomer of ArH and either syn or anti isomer of CH=N), 7.62 (t, about 0.5H, peak of either syn or anti isomer of CH=N), 7.8, 8.2 (both s,br,total IH,N=OH)

EXAMPLE 5

2-[2,3-Dimethyl-4-(2-methoxyethyl)phenoxy]-acetaldehyde oxime

Colorless solid, m.p. 84°–85° C., yield 90%

Proton NMR ($\delta$, CDCl$_3$): 2.15–2.25 (4 peaks according to syn-anti isomers,6H,ArCH$_3$), 2.90 (t,2H,ArCH$_2$), 3.35(s,3H,OCH$_3$), 3.52(t,2H,MeOCH$_2$), 4.51, 4.87 (both d, total 2H, CHHD 2—CH=N), 6.65 (t,lH,ArH), 6.98 (d,lH,ArH), 7.05, 7.65 (both t, total IH,CH=N), 8.25, 8.62 (s,br,total IH,N-OH)

EXAMPLE 6

2-[4-(2-Ethoxyethyl)phenoxy]-acetaldehyde oxime

Colorless solid, m.p. 78°–80° C. (melted partially at 66°–70° C.), yield 86%.

Proton NMR ($\iota$, CDCl$_3$): 1.22 (t,3H,—CH$_3$), 2.85 (t,2H,ArCH$_2$), 3.51 (q,2H,Me—CH$_2$), 3.60(t,2H,Ar-C—CH$_2$—O), 4.65, 4.89 (both d, total 2H, CH$_2$CH=N), 6.8–6.9 (two sets of d,2H,ArH), 7.1–7.2 (two sets of d,2H,ArH), 7.02, 7.62 (both t, total IH, CH=N), 8.12, 8.42 (both s,br,total 1H, n—OH)

EXAMPLE 7

2-[4-(2-Methoxyethyl)phenoxy]-acetaldehyde oxime

Colorless solid, m.p. 48°–50° C. (melted partially at 42°–45° C.), yield 88 %.

Proton NMR ($\delta$, CDCl$_3$): 2.84 (t,2H,ArCH$_2$), 3.38 (s,3H,OCH$_3$), 3.6 (two sets of t,total 2H,CH$_2$—OMe), 4.61, 4.89 (both d, total 2H,CH$_2$—C=N), 6.8–6.9 (2 sets of d, total 2H, ArH), 7.1–7.2 (two sets of d,lH,ArH), 7.02–7.52 (both d,total 1H,CH=N), 8.95, 9.30 (both s,br,total 1H,NOH)

EXAMPLE 8

2-[2,6-Dimethyl-4-(2-ethoxyethyl)phenoxy]-acetaldehyde oxime

Pale yellow oil, yield 92%.

Proton NMR ($\delta$, CDCl$_3$ ): 1.22 (t,3H,CH$_2$—CH$_3$), 2.26 (s,6H,ArCH$_3$), 2.80 (t,2H,ArCH$_2$), 3.52(q,3H,OCH$_2$CH$_3$), 3.60 (t,2H,ArCH$_2$CH$_2$), 4.40, 4.68 (respectively d,total 2H,CH$_2$C=N, according to syn-anti isomers), 6.85 (s,2H,ArH), 7.17, 7.68 (respectively t,total 1H,—CH=N, according to syn-anti isomers), 8.13, 8.4 (s,br,total 1H,N=OH)

REFERENCE EXAMPLE

Substituted phenoxyacetaldehyde dialkylacetals which are the starting materials were prepared from the corresponding p-bromophenoxyacetaldehyde dialkylacetals according to the following example, respectively

1-(2,2-Dimethoxyethoxy)-4-(2-ethoxyethyl)-2,3-dimethylbenzene

Grignard reaction was carried out in conventional manner from 5.0 g of 4-bromo-1-(2,2-dimethoxyethoxy)-2,3dimethylbenzene and 0.5 g of magnesium in 30 ml of tetrahydrofuran, and then 1.0 g of ethylene oxide was blown into the reaction mixture at 50° C. Further, the mixture was stirred at the same temperature for 2 hours. Tetrahydrofuran was removed under reduced pressure, and 50 ml of toluene and 50 ml of 1 N hydrochloric acid were added. The organic layer separated was washed with water, and then 5 ml of 20% sodium hydroxide, 4.0 g of diethylsulfate and 0.3 g of tetrabutylammonium chloride were added, followed by heating and stirring at 40° C. for 5 hours. After cooling, the toluene layer was washed with water, dried and then concentrated under reduced pressure The residual oil was purified by column chromatography (Wako Gel C-200, eluant: n-hexane ethyl acetate=10:1) to obtain 3.5 g of the title product.

Other starting materials were also similarly synthesized. However, when methoxyethyl derivatives were prepared (Examples 3, 5, 7), dimethylsulfate was used in place of diethylsulfate.

The respective starting materials were identified by proton NMR spectrum.

COMPARATIVE EXAMPLE

According to the method described in Japanese Unexamined Patent Publication No. 260054/1986, 1-(2,2-dimethoxy-ethoxy)-4-(2-ethoxyethyl)-2,3-dimethylbenzene was reacted with hydroxylamine sulfate. The yield was found to be 5% or less even after 6 hours.

Similarly, the reaction was carried out using hydroxylamine hydrochloride. The yield was found to be 65% after 4 hours, and the product was not crystallized due to very much by-products and must be purified by column chromatography (conversion was approximately 100 %).

EXAMPLE 9

Into a 20-liter autoclave charged were Raney nickel prepared (50 g as 50% alloy), 10 liters of methanol and 1.5 kg of liquid ammonia. After the hydrogen pressure was adjusted to 20 atm., the mixture was heated to 100° C. with stirring and stirred for one hour Into the mixture of activated Raney nickel thus obtained was charged 820 g of 2-[2,3-dimethyl-4-(2-ethoxyethyl)-phenoxy]-acetaldehyde oxime. Hydrogen was introduced until 20 atm., and the mixture was heated and stirred at 100° C. Absorption of hydrogen began at around 80° C. When the pressure was lowered, hydrogen was introduced to maintain the pressure at 20 atm. After about 0.5 to 2.5 hours, theoretical amount of hydrogen was absorbed, and then after cooling and releasing pressure, the catalyst was removed by filtration through a Nutze having Celite The filtrate was concentrated under reduced pressure to obtain a crude product. Yield 85-93%. The crude product was purified by distillation to obtain 2-[2,3-dimethyl-4-(2-ethoxyethyl)-phenoxy]ethylamine (boiling point 170°-175° C./1 mmHg).

Raney nickel was prepared according to the following method. Fifty grams of 50% Raney nickel alloy was added into one liter of an aqueous 30% by weight of sodium hydroxide solution so that the temperature was maintained at 80°to 90° C. After completion of the addition, the mixture was stirred at 80° C. for one hour and washed repeatedly with distilled water until pH of washing was around 7 (500 ml×15). Subsequently, the catalyst was washed wilh methanol repeatedly (500 ml ×5) before use.

EXAMPLE 10

Example 9 was repeated on a scale of 1/100 thereof except that triethylamine was employed in place of liquid ammonia. Yield 88%.

EXAMPLE 11

Example 9 was repeated on a scale of 1/50 thereof except that the amount of liquid ammonia was 4 g. Yield 85%.

EXAMPLES 12 to 14

Example 9 was repeated except that the amount of Raney nickel (as 50% alloy) was changed as follows.

| Example | Raney nickel (g) | Yield % |
| --- | --- | --- |
| 12 | 8.2 | 70 |
| 13 | 82 | 88 |
| 14 | 120 | 93 |

EXAMPLES 15, 16 and 17

Example 9 was repeated except that the sodium hydroxide concentration during preparation of Raney nickel was changed as follows.

| Example | NaOH conc. (%) | Yield % |
| --- | --- | --- |
| 15 | 20 | 81 |
| 16 | 10 | 87 |
| 17 | 40 | 83 |

EXAMPLE 18

For the purpose of recycling Raney nickel, after completion of the reaction in Example 9, 85 % of the reaction mixture was removed by decantation (the catalyst was not removed so far as possible), and newly 8.5 liters of a 15% methanolic ammonia suspension of 2-[2,3-dimethyl-4-(2-ethoxyethyl)-phenoxy]-acetaldehyde in equal amount to the initial amount was charged, and again hydrogen was injected to 20 atm. to carry out the reaction. This operation was repeated for 6 times. The yields for the respective operations were found to be 88 % for the first, 83 % for the second, 82 % for the third, 80 % for the fourth, 80 % for the fifth and 81 % for the sixth.

EXAMPLES 19 to 27

As the oximes (II), the following compounds were allowed to react similarly as in Example 9 on a scale of 1/100 thereof. Corresponding substituted phenoxyethylamines (III) were obtained.

| Example | $R^1$ | $R^2$ | $R^3$ | Yield % |
| --- | --- | --- | --- | --- |
| 19 | 2-Et | H | —CH$_2$CH$_2$OEt | 80 |
| 20 | 2-Me | 3-Me | H | 85 |
| 21 | 2-Me | 3-Me | —CH$_2$CH$_2$OH | 77 |
| 22 | 2-Me | 5-Me | —CH$_2$CH$_2$OEt | 84 |
| 23 | 2-Me | 6-Me | —CH$_2$CH$_2$OEt | 81 |
| 24 | 2-Me | 3-Me | —CH$_2$CH$_2$OMe | 85 |
| 25 | H | H | —CH$_2$CH$_2$OEt | 75 |
| 26 | H | H | —CH$_2$CH$_2$OMe | 78 |
| 27 | H | H | H | 81 |

Each product was purified by column chromatography (Kieselgel 60, eluant: methanol:ethyl acetate=1:3), and identified by proton NMR spectrum

EXAMPLE 28

Example 9 was repeated on a scale of 1/50 thereof except that the hydrogen pressure during the reaction was made 70 atm. Yield 93%.

EXAMPLES 29

Example 9 was repeated on a scale of 1/50 thereof except that the hydrogen pressure during the reaction was made 50 atm. Yield 90%.

EXAMPLE 30

Example 25 was repeated except that a stabilized nickel was used in place of Raney nickel. In this case, no activation operation was conducted. Yield 65%.

EXAMPLE 31

Example 9 was repeated on a scale of 1/50 thereof except that a catalyst containing 2% chromium in Raney nickel was used. Yield 82%.

COMPARATIVE EXAMPLE 2

When Example 9 was repeated on a scale of 1/50 thereof by use of 2 g of 5% palladium-carbon in place of Raney nickel, no desired product was formed at all, but by-products were formed in a large amount.

COMPARATIVE EXAMPLE 3

When Example 9 was repeated on a scale of 1/50 thereof by use of 2 g of 5% palladium-carbon in place of Raney nickel and 5% ethanolic hydrochloric acid as the solvent, the hydrochloride of the desired product was obtained in 50% yield.

COMPARATIVE EXAMPLE 4

Example 9 was practiced on a scale of 1/50 thereof by use of Raney cobalt in place of Raney nickel. The desired product was obtained in 60% yield.

We claim:

1. A substituted phenoxyacetaldehyde oxime of the formula:

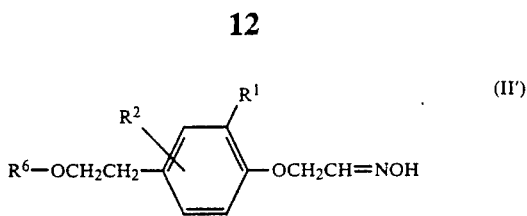

wherein $R^1$, and $R^2$ each represent a hydrogen atom or a lower alkyl group and $R^6$ is a hydrogen atom or a lower alkyl group.

2. The substituted phenoxyacetaldehyde oxime according to claim 1, wherein the lower alkyl group represented by $R^1$, $R^2$ and $R^6$ is selected from the group consisting of methyl group, ethyl group and propyl group.

3. The substituted phenoxyacetaldehyde oxime according to claim 1, wherein the substituted phenoxyacetaldehyde oxime is 2-(2,3-dimethyl-4-(2-ethoxyethyl)phenoxy)acetaldehyde oxime.

4. The substituted phenoxyacetaldehyde oxime according to claim 1, wherein the substituted phenoxyacetaldehyde oxime is 2-(2,5-dimethyl-4-(2-ethoxyethyl)phenoxy)acetaldehyde oxime.

5. The substituted phenoxyacetaldehyde oxime according to claim 1, wherein the substituted phenoxyacetaldehyde oxime is 2-(2,6-dimethyl-4-(2-methoxyethyl)phenoxy)acetaldehyde oxime.

6. The substituted phenoxyacetaldehyde oxime according to claim 1, wherein the substituted phenoxyacetaldehyde oxime is 2-(2-ethyl-4-(2-ethoxyethyl)phenoxy)acetaldehyde oxime.

7. The substituted phenoxyacetaldehyde oxime according to claim 1, wherein the substituted phenoxyacetaldehyde oxime is 2-(2-ethyl-4-(2-ethoxyethyl)phenoxy)acetaldehyde oxime.

8. The substituted phenoxyacetaldehyde oxime according to claim 1, wherein the substituted phenoxyacetaldehyde oxime is 2-(4(2-ethyoxyethyl)phenoxy)acetaldehyde oxime.

9. The substituted phenoxyacetaldehyde oxime according to claim 1, wherein the substituted phenoxyacetaldehyde oxime is 2-(4-(2-methoxyethyl)phenoxy)acetaldehyde oxime.

10. The substituted phenoxyacetaldehyde oxime according to claim 1, wherein the substituted phenoxyacetaldehyde oxime is 2-(2,6-dimethyl-4-(2-ethoxyethyl)phenoxy)acetaldehyde oxime.

* * * * *